United States Patent
Carmody et al.

(10) Patent No.: US 8,251,099 B2
(45) Date of Patent: Aug. 28, 2012

(54) CHECK VALVE

(75) Inventors: Colm Carmody, Co. Kerry (IE); Kieran Costello, Co. Clare (IE); Brendan Casey, Co. Tipperary (IE)

(73) Assignee: Illinois Tool Works Inc., Glenview, IL (US)

( * ) Notice: Subject to any disclaimer, the term of this patent is extended or adjusted under 35 U.S.C. 154(b) by 13 days.

(21) Appl. No.: 12/745,515

(22) PCT Filed: Jan. 22, 2009

(86) PCT No.: PCT/IB2009/000106
§ 371 (c)(1),
(2), (4) Date: May 28, 2010

(87) PCT Pub. No.: WO2009/093126
PCT Pub. Date: Jul. 30, 2009

(65) Prior Publication Data
US 2010/0300556 A1 Dec. 2, 2010

(30) Foreign Application Priority Data
Jan. 24, 2008 (DE) .................. 20 2008 001 077 U

(51) Int. Cl.
*F16K 15/14* (2006.01)
(52) U.S. Cl. .................. 137/859; 604/247; 137/852
(58) Field of Classification Search ............ 137/512.15, 137/859, 843, 852; 604/247
See application file for complete search history.

(56) References Cited

U.S. PATENT DOCUMENTS

| 4,718,456 A * | 1/1988 | Schoonover ............ 137/625.37 |
| 2005/0075612 A1 | 4/2005 | Lee et al. |
| 2007/0163664 A1 * | 7/2007 | Mijers et al. .................. 137/859 |
| 2008/0087859 A1 * | 4/2008 | Enerson et al. ............ 251/149.7 |

FOREIGN PATENT DOCUMENTS

| DE | 19723648 C1 | 8/1998 |
| DE | 202004009358 U1 | 9/2004 |
| DE | 202006016730 U1 | 1/2007 |
| EP | 0612537 A2 | 8/1994 |
| GB | 690897 A | 4/1953 |

OTHER PUBLICATIONS

ISR for PCT/IB2009/000106 dated Jul. 7, 2009.

* cited by examiner

*Primary Examiner* — Kevin Lee
*Assistant Examiner* — Macade Brown
(74) *Attorney, Agent, or Firm* — Lowe Hauptman Ham & Berner LLP

(57) ABSTRACT

A check valve in particular for medical applications has a first hose connecting casing and a second hose connecting casing and a membrane disk configured between the two hose connecting casings. The membrane disk is made of a resilient material and cooperates with an annular valve seat. The membrane disk is fitted radially outside the valve's seat with apertures leading to a discharge space. The wall of the second hose connecting casing is opposite the apertures and fitted with a surface curved away from the membrane toward the discharge channel. The discharge channel is fitted with an intake mouth in the wall, and conically tapers within a transition segment toward the intake mouth. Recesses communicating with the discharge space are fitted into the transition segment and are dimensioned in a way to substantially compensate the different flow cross-sections between the intake mouth and the discharge channel.

8 Claims, 4 Drawing Sheets

CHECK VALVE

RELATED APPLICATIONS

The present application is national phase of International Application Number PCT/IB2009/000106, filed Jan. 22, 2009, and claims priority from, German Application Number 202008001077.2, filed Jan. 24, 2008, the disclosures of which are hereby incorporated by reference herein in their entirety.

BACKGROUND

The present invention relates to a check valve, in particular for medical applications, which comprises a first and a second hose connecting casing and a resilient membrane disk that is configured between said casings and that, in the event of excess pressure in an intake channel of the first hose connecting casing can be lifted off an annular valve seat enclosing an surrounding intake space communicating with said intake channel and that, in the event of excess pressure in a discharge channel of the second hose connecting casing, can be pressed reliably and in a minimum of time onto the valve seat, this membrane disk being fitted at its outer periphery with an annular bead received in mutually opposite annular grooves of the hose connecting casings, the membrane disk being fitted radially outside said valve seat and above an annular space surrounding the same with apertures running to a discharge space and the wall of the second hose connecting casing's wall opposite said apertures being fitted with recesses that communicate with the said discharge channel.

Such a check valve is already known from the applicant's earlier disclosure in the German Gebrauchsmuster 20 2004 009 358.8.

Such check valves are needed in medical practice in the conduits of infusion systems, diagnostic apparatus, intravenous hose conduits and the like, and consequently they must close very reliably and their time of closure must be kept within fractions of a second to preclude any reflux of liquids contaminated with undesirable substances. At the same time the manufacture of such check valves must be extremely economical as well as being very accurate when considered statistically, such valves in medical practice being exclusively used as one-way means (non-return articles) and their economically required manufacture entailing automated mass prochannelion. At the same time there are rigorous statutory requirements to assure unvarying and uniform operation, and observance of statutory requirements being monitored for instance in Germany by the Technischen Überwachungsverein (Technical Monitoring Service). Such medical check valves are sanctioned only following appropriate positive test results.

The above defined check valve improves one of an earlier disclosure of applicant in the European patent document 0 612 537. This known valve on one hand fully meets the above cited requirements because its design calls for grooves receiving the annular bead at the periphery of the membrane disk in such a way that when assembling the two hose connecting casings, the said membrane disk shall be subjected to radial tractions allowing adjusting the tension in the membrane, as a result of which the check valve may be made even more quickly and reliably responsive. On the other hand practical operation of this known valve has shown that higher pressures at the check valve's intake side my entail the membrane apertures coming to rest against the opposite wall of the discharge space, thus causing unintended closure of an open check valve.

To remedy this unintended behavior of the membrane and unintended valve closure, another feature of the aforementioned valve is used, namely the second hose connecting casing's wall opposite said apertures has been fitted at said check valve's discharge side with recesses communicating with the discharge channel and configured as an annular channel of a radius corresponding to the radius at which the apertures are configured in the membrane disk. This design features ensures that even if due to high pressures the membrane disk were to be entirely forced against the discharge space's wall, nevertheless the desired flow cross-section shall be preserved, this flow taking place through the annular channel to the discharge side.

Practical operation of the above check valve however has shown that even the above improved design may be sometimes inadequate in the presence of high pressures due to the membrane being distorted so much in this process that the total available open flow cross-section might then be reduced. Another difficulty encountered at high pressures is that after high-pressure relief, the membrane might be excessively stressed and thereby no longer sealing adequately while at the same time the opening pressure has been considerably lowered.

A further improvement to the above check-valve difficulties was attained by means of the design disclosed in applicant's patent document DE GM 20 2006 016 730.7 (Gebrauchsmuster), namely in that the recesses on the membrane disk's discharge side be separated from each other by support faces, the recesses communicating through narrow, deep grooves with the discharge channel. The recess-fitted support faces assume the shape of a kind of crown-shaped protrusion from the second hose connecting casing's opposite wall, which supports the membrane when the valve is opened.

With respect to a check valve of the kind defined above, it is the objective of the present invention to even further improve it relative to the state of the art, namely allowing much higher operational pressures in spite of a low opening pressure.

SUMMARY

This goal basically is attained regarding a valve of the initially cited design in that the second hose connecting casing's wall opposite the apertures is provided with a curvature directed from the membrane disk 1 the direction of the discharge channel, further that the discharge channel in the wall comprises an intake opening of which the diameter is less than that of the discharge channel, in that the discharge channel tapers conically within a transition zone toward the intake opening, and in that the transition zone comprises recesses communicating with the discharge space and dimensioned in a way that the differential flow cross-section between the intake opening and the discharge channel is basically compensated.

This configuration offers the advantage that the valve can tolerate much higher operational pressures because the membrane disk may come to rest by means of a large area against the opposite wall while assuming a limited convex shape, as a result of which both a rechannelion of the available flow cross-section and excessive membrane stretching are precluded. Said rest area available to the membrane is substantially increased on account of the reduced diameter of the intake opening to the discharge channel, while the discharge channel's flow cross-section is nevertheless preserved by the compensating effect of the recesses.

In a particularly preferred embodiment mode of the present invention, the intake opening diameter is about half the discharge channel's diameter. In this manner the maximally possible large rest area is available to the membrane without adverse effects on the check valve flow.

Moreover the present invention may be further improved by such details as the wall enclosing the intake opening being smooth, without protrusions or the like, and merging into the intake opening at a given radius. In this manner, at high operational pressures, the membrane may be supported in especially stress-free manner.

In detail it is further preferred that the recesses shall be slots surrounding in a stellate pattern the intake opening and the transition zone.

This embodiment mode may be advantageously extended in that said slots are fitted with an upper wall rising from the discharge space's top wall toward the top end of the transition zone. This feature offers the advantage that the flow is directed from the discharge space diagonally upward into the discharge channel and consequently turbulence arises little if at all.

Regarding the same objective, preferably the slots flare from the discharge space to the transition zone.

In particular the discharge channel preferably shall flare at a low conic angle from the transition zone's top end to its discharge. This feature promotes especially advantageous flow In a further preferred embodiment of the present invention, the membrane disk is fitted with a circular reinforcement opposite the intake opening, the diameter of said reinforcement approximately corresponding to that of the top end of transition zone. This feature offers the advantage that the membrane is additionally reinforced at its zone opposite the intake opening, namely the zone not supported when in the presence of high pressures, and said reinforcement in turn precluding degrading membrane deformations in this area too.

BRIEF DESCRIPTION OF THE DRAWINGS

The invention is elucidated below by means of an embodiment mode illustrated in the appended Figures.

DETAILED DESCRIPTION

Figure 1:
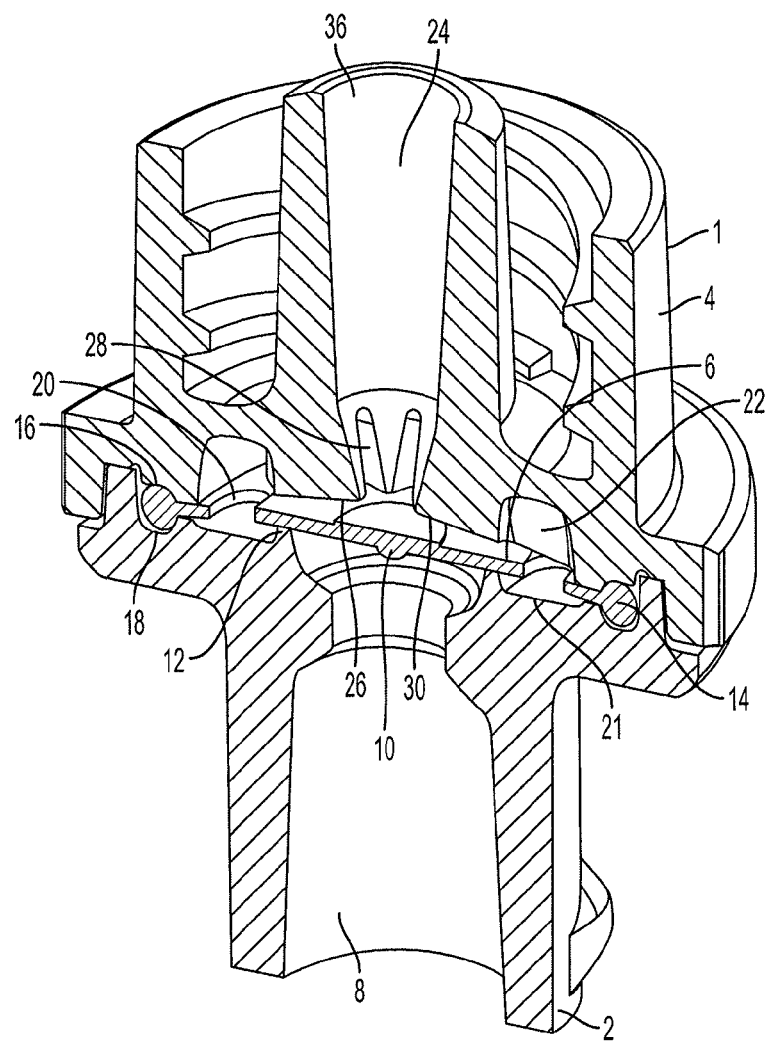
FIG. 1 is a perspective schematic section of an embodiment mode of the check valve of the present invention when in its closed state.

The illustrative check valve 1 shown in the appended Figures is especially appropriate for medical applications and relates to pressure differentials, for instance from very high pressures to as low as 0.002 bars. The check valve 1 is constituted by three components, namely a first hose connecting casing 2 and a second hose connecting casing 4 and also a membrane disk 6 which is positioned between the two hose connecting casings 2 and 4, and which is illustratively made of a flexible plastic, for instance silicone. The hose connecting casings 2 and 4 are made from a plastic for instance by injection molding and are connected to each other following insertion of the membrane disk 6 by conventional connection procedures such as ultrasonic welding, bonding and the like.

The first connecting casing 2 is fitted with an intake channel 8 entering an intake space 10. Opposite the membrane disk 6, the intake chamber 10 is surrounded by an annular valve seat 12, the membrane disk 6 being prestressed against said seat. The membrane disk 6 comprises a continuously closed central part to transmit substantial tensional forces radially from center to circumference and vice versa and is fitted at its outer peripheral zone with an annular bead 14 for instance integrated by injection molding into the membrane disk 6. The first hose connecting casing 2 comprises an annular groove 16 in said first casing's end face and wherein an annular groove 18 is opposite the annular groove 16 of the second hose connecting casing 4 when in their assembled state. When assembling the two hose connecting casings 2, and 4, the annular bead 14 is received in the mutually opposite annular grooves 16 and 18 and is simultaneously prestressed against the valve seat 12.

Figure 2:
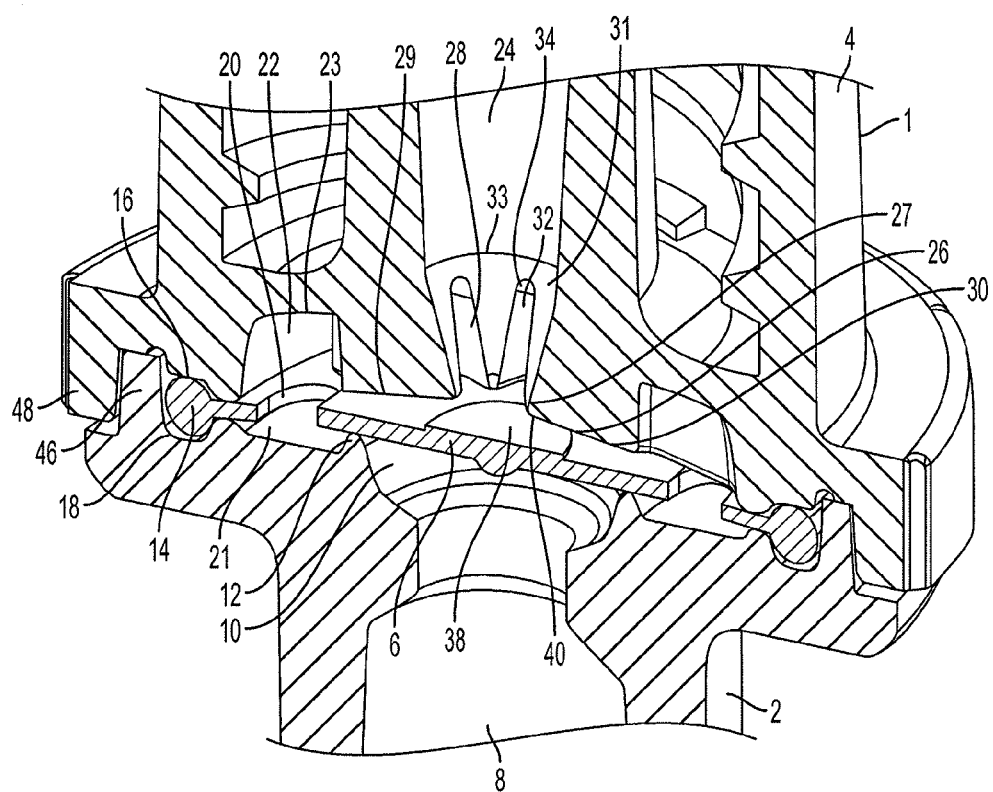
FIG. 2 is a much enlarged detail of the valve of FIG. 1.

As shown most clearly in FIG. 2, radially outside the valve seat 12, the membrane disk 6 is fitted with apertures 20 positioned on a circular radius, that are configured above an annular space 21 of the first hose connecting casing 2 which is situated radially outside said valve seat 12. The apertures 20 connect the annular space 21 of the first hose connecting casing 2 to an annular discharge space 22 of the second hose connecting casing 4 above the membrane 6. The discharge space 22 in the second hose connecting casing 4 communicates with the discharge channel 24 of the second hose connecting casing 4 in the manner elucidated further below.

Radially inside its annular structure, the discharge space 22 comprises a wall 26 which is opposite the membrane disk 6 and which is having a curvature 29 away from the membrane disk 6 toward the discharge channel 24.

The discharge channel 24 is fitted with an intake opening 27 that is situated in the wall 26 approximately at the apex of the curvature 29 and that, as shown by the drawings, exhibits a smaller diameter than that of the discharge channel 24. The discharge channel 24 conically tapers along a transition section 31 (FIGS. 2 through 4) toward the intake opening 27. The curvature 29 is forming a supporting surface 30 for the membrane disk 6.

As shown in the drawings, the diameter of the intake opening 27 is dimensioned in a way to be about half that of the discharge channel 24. This feature substantially increases the supporting surface 30 available to the membrane 6, as a result of which the check valve of the present invention may operate at high pressures without thereby in any way damaging the membrane disk 6.

In order to attain a constant flow cross-section between the intake opening 8 and the discharge channel 24 despite the reduction of the intake opening 27, the transition section 31 is fitted with the recesses 28 communicating with the discharge space 22, these recesses being dimensioned in a way that the cross-sectional flow differential between the intake opening 27 and the discharge channel 24 shall have been substantially compensated. In this manner, despite the substantial enlargement of the supporting area 30, the flow characteristic of the check valve 1 is preserved.

As indicated, the preferred embodiment of the present invention calls for the diameter of the intake opening 27 to approximately correspond to half the diameter of the discharge channel 24.

The wall 26 enclosing the intake opening 27 is devoid of any protrusions and the like and merges at a radius 40 into said intake opening. Due to this design, the membrane disk 6 is freely displaceable during the opening procedure, allowing operating at minimal opening pressures.

Figure 3:
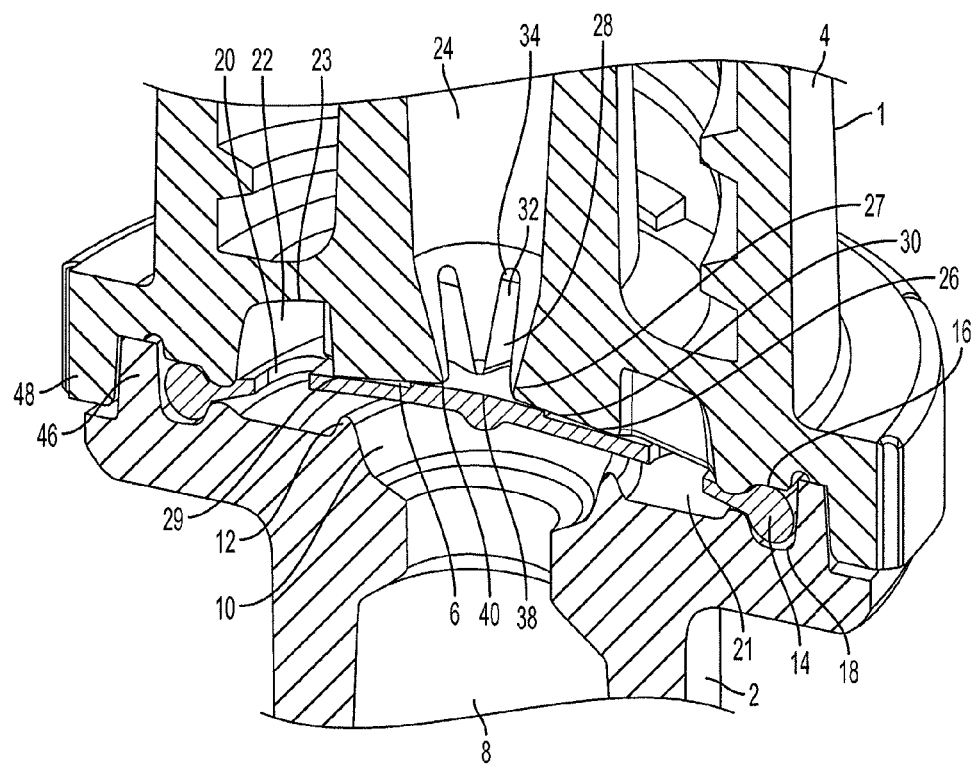
FIG. 3 is a view corresponding to that of FIG. 2 of the valve of FIG. 2 in its open state.
Figure 4:
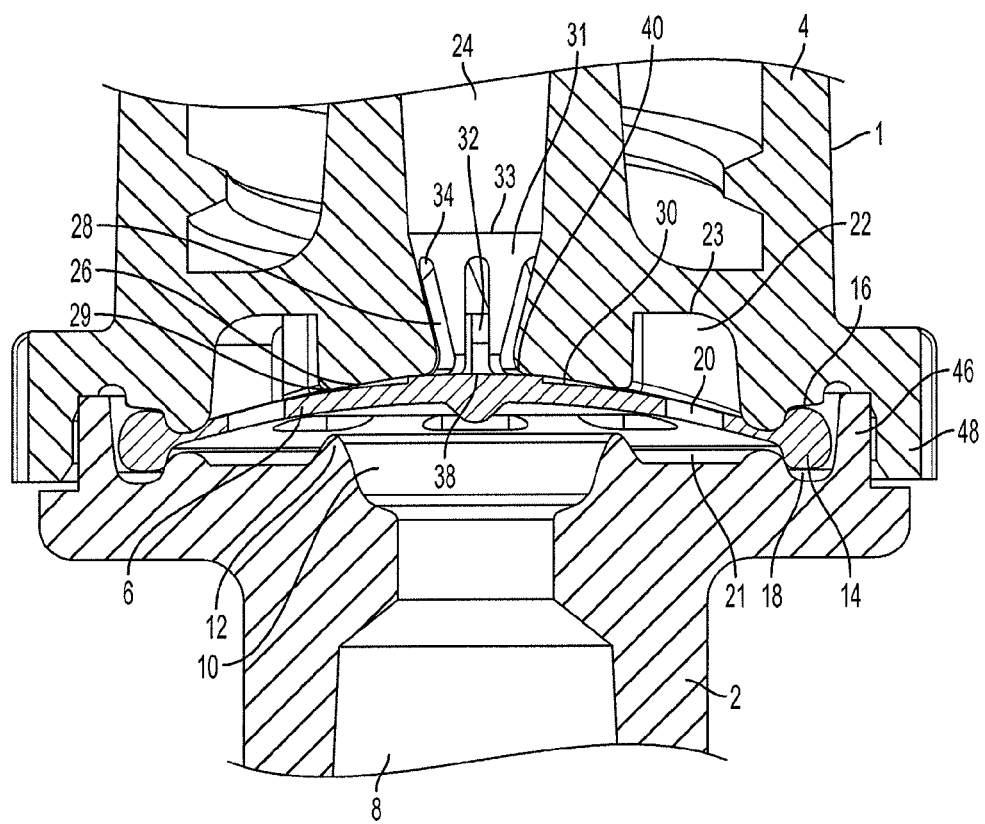
FIG. 4 is a sectional elevation of FIG. 3.

As shown in FIGS. 2 through 4, the preferred embodiment mode's recesses 28 are slots 28 enclosing in a stellate manner the intake opening 27 and the transition section 31. The slots 32 comprise an upper wall 34 rising from the top wall 23 of the discharge space 22 toward the top end 33 of the transition section 31. Concurrently the slots 32 flare from the discharge space 22 in the direction of the transition section 31. This design offers especially advantageous flow conditions.

For the same reason the discharge channel 24 increasing with a small conicity from the top end 33 of the transition section 31 toward the discharge 36.

Due to the fact that at high pressures, the membrane disk 6 is coming into engagement with the wall 26 respectively its supporting surface 30 as illustrated in FIGS. 3 and 4 only the central zone of the membrane disk 6 is wholly devoid of support. To avert that in such a case the applied high pressures should excessively deform the membrane disk 6, the membrane disk 6 of the preferred embodiment mode of the present invention is fitted opposite the intake opening 27 with a circular reinforcement 38 of which the diameter approximately corresponds to that of the top end 33 of the transition section 31.

To assemble the check valve, the two hose connecting casings 2 and 4 may be connected to each other by means of an inner annular protrusion 46 at the first casing and by an external annular protrusion 48 at the second casing 4, where, as indicated by the drawings, the annular protrusions 46 and 48 engage each other. The final connection is implemented for instance by ultrasonic welding and bonding.

All features and advantages, implicit and explicit, of the specification, the claims and drawings, inclusive design details and spatial configurations, may be construed being inventive per se or in arbitrary combinations.

The invention claimed is:

1. A check valve, comprising:
   a first hose connector housing;
   a second hose connector housing; and
   a diaphragm disk positioned between the hose connector housings, the diaphragm disk being made of a flexible material, the diaphragm disk being configured to be
      lifted from an annular valve seat surrounding an inlet space connected with an entry channel during a first period when a pressure at the entry channel is greater than a pressure at an exit channel, and
      pressed onto the valve seat during a second period when the pressure at the entry channel is lower than the pressure at the exit channel,
   wherein
   the diaphragm disk has an annular bead at an outer circumferential area, the annular bead being received in opposed annular grooves of the hose connector housings, the diaphragm disk located radially outwardly of the valve seat being provided with openings leading to an exit space;
   a wall of the second hose connector housing opposite to the openings has recesses connected to the exit channel,
   the wall of the second hose connector housing opposite to the openings has a curvature directed away from the diaphragm disk in the direction of the exit channel, the curvature being configured to cause the wall of the second hose connector the diaphragm disk to contact during the first period when the pressure at the entry channel is greater than the pressure at the exit channel,
   the exit channel has an entry opening in the wall, a diameter of the entry opening being smaller than that of the exit channel,
   the exit channel is tapering conically toward the entry opening in a transition section, and
   the recesses are provided in the transition section and are connected with the exit space, said recesses being dimensioned such that a cross-sectional flow differential between the entry opening and the exit channel is substantially compensated.

2. The check valve according to claim 1, wherein the diameter of the entry opening is about half of the diameter of the exit channel.

3. The check valve according to claim 1, wherein the wall surrounding the entry opening is smooth and without projections and is merging into the entry opening with a radius.

4. The check valve according to claim 1, wherein the recesses are slots surrounding the entry opening and the transition section in a star-shaped pattern.

5. The check valve according to claim 4, wherein each of the slots has a top wall which is rising from the top wall of the exit space in the direction of a top end of the transition section.

6. The check valve according to claim 4, wherein each of the slots is enlarged from the exit space to the transition section.

7. The check valve according to claim 1, wherein the exit channel starting from the top end of the transition section is enlarged toward the exit channel with conicity.

8. The check valve according to claim 1, wherein the diaphragm disk opposite to the entry opening has an annular reinforcement, the diameter of which is corresponding to the diameter of a top end of the transition section.

* * * * *